(12) United States Patent
Zander et al.

(10) Patent No.: US 7,745,224 B2
(45) Date of Patent: Jun. 29, 2010

(54) PROCEDURE FOR THE STANDARDIZATION OF COAGULATION TESTS

(75) Inventors: Norbert Zander, Marburg (DE); Matthias Wilkens, Marburg (DE)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 1049 days.

(21) Appl. No.: 11/452,966

(22) Filed: Jun. 15, 2006

(65) Prior Publication Data

US 2007/0020765 A1 Jan. 25, 2007

(30) Foreign Application Priority Data

Jun. 16, 2005 (DE) ........................ 10 2005 028 018

(51) Int. Cl.
G01N 33/86 (2006.01)
(52) U.S. Cl. ...................... 436/69; 436/63; 435/13; 600/369; 73/64.41
(58) Field of Classification Search ............. 436/63, 436/69, 8, 16, 18; 435/2, 13; 422/61; 600/369; 73/64.41
See application file for complete search history.

(56) References Cited

U.S. PATENT DOCUMENTS

| | | | |
|---|---|---|---|
| 4,067,777 A | | 1/1978 | Innerfield et al. |
| 4,301,028 A | | 11/1981 | Bartl et al. |
| 4,946,775 A | | 8/1990 | Yin |
| 5,525,477 A | * | 6/1996 | Hassouna ............... 435/13 |
| 5,670,329 A | | 9/1997 | Oberhardt |
| 5,866,425 A | * | 2/1999 | Woodhams et al. ......... 436/16 |
| 2001/0004641 A1 | * | 6/2001 | Hawkins ................ 514/560 |
| 2005/0136499 A1 | | 6/2005 | Henckel |

FOREIGN PATENT DOCUMENTS

| | | |
|---|---|---|
| DE | 29 03 701 B1 | 2/1980 |
| DE | 695 21 470 T2 | 5/2002 |
| EP | 0 014 039 | 8/1980 |
| EP | 0 217 768 A2 | 4/1987 |
| EP | 0 562 425 A1 | 9/1993 |
| EP | 706 658 B1 | 4/1996 |
| EP | 0 743 521 A2 | 11/1996 |
| EP | 1 544 621 A1 | 6/2005 |

OTHER PUBLICATIONS

European Search Report for Patent Application No. 06010455.1-2404, dated Aug. 4, 2006.
Adcock, D.M., et al., "Enhanced standardization of the International Normalized Ratio through the use of plasma calibrants; a concise review," *Blood Coagulation and Fibrinolysis*, 2000, 11(7):583-590.
Brien, W.F., et al., "In-house Calibration of the International Sensitivity Index or Calibration Curve for Determination of the International Normalized Ratio," *Arch Pathol Lab Med*, Mar. 2004, 128:308-312.
Talstad I., "Why is the Standardization of Prothrombin Time a Problem?.," *Haemostasis*, 2000, 30:258-267.
Brill-Edwards et al., "Establishing a Therapeutic Range for Heparin Therapy," *Annals of Internal Medicine* 119(2):104-109 (1993).
Nelson, "Current Considerations in the Use of the APTT in Monitoring Unfractionated Heparin," *Clinical Laboratory Science* 12(6):359-364 (1999).
Olsen et al., "College of American Pathologists Conference XXXI on Laboratory Monitoring of Anticoagulant Therapy, Laboratory Monitoring of Unfractionated Heparin Therapy," *Archives of Pathology and Laboratory Medicine* 122:782-798 (1998).
Reed et al., An Attempt to Standardize the APTT for Heparin Monitoring, Using the P.T. ISI/INR System of Calibration, Results of a 13 Centre Study, *Thrombosis Research* 74(5):515-522 (1994).
Van Der Velde et al., "The APTT Monitoring of Heparin—The ISTH/ICSH Collaborative Study," *Thrombosis and Haemostasis* 73(1)73-81(1995).

* cited by examiner

*Primary Examiner*—Maureen M Wallenhorst
(74) *Attorney, Agent, or Firm*—Finnegan, Henderson, Farabow, Garrett and Dunner, L.L.P.

(57) ABSTRACT

The present invention lies in the field of coagulation diagnosis and relates to a procedure for the standardization of coagulation tests, where calibrators are used to which a discrete standard coagulation time is assigned. The procedure is particularly suitable for the standardization of prothrombin time, activated partial thromboplastin time, thrombin time, ecarin time or batroxobin time.

11 Claims, 1 Drawing Sheet

PROCEDURE FOR THE STANDARDIZATION OF COAGULATION TESTS

This application claims priority to German Patent Application No. 10 2005 028 018.8, filed Jun. 16, 2005, which is incorporated herein by reference.

The present invention lies in the field of coagulation diagnosis and relates to a procedure for the standardization of in vitro coagulation tests.

Coagulation tests make possible the measurement of the activity of a single or a number of coagulation factors by the measurement of the fibrin formation rate in vitro, i.e. outside the human or animal body (coagulometry). The primary result of these tests is a coagulation time which is customarily measured in seconds from the time of addition of an activator and/or of $Ca^{2+}$ ions to the sample or to the sample mixture until the formation of a detectable fibrin clot. A coagulation time is also a measure of the hemostatic potential, the coagulability, of a sample, where the influences of all coagulation-promoting and anticoagulation factors and substances which are contained in the sample and which are determined by the respective test come to bear.

Coagulation times can be determined by manual or automatic procedures. In the case of the automatic determination, the measurement of a mechanical or of an optical property of the sample/reagent mixture, e.g. the viscosity or turbidity, is very widespread. In all cases of automatic measurement, a property of the sample/reagent mixture is continuously measured, and the coagulation time can be determined as an end point from the time-dependent change in the property with the aid of evaluation procedures.

Typical examples of coagulation tests of this type are the prothrombin time (PT), which is also called the Quick test or thromboplastin time, the activated partial thromboplastin time (APTT), the thrombin time (TT), the batroxobin time (BT) or the ecarin time (ECT). These tests and their variants are usually used for screening for defects in a sub-range of the coagulation system (screening tests, global tests, search tests) or for the activity measurement of individual factors. [Overview in Barthels, N. and von Depka, N.: Das Gerinnungskompendium (The Coagulation Compendium), Georg Thieme Verlag Stuttgart, 2003]. The defects of the coagulation system which can result in a proneness to bleeding or a proneness to thrombosis include, for example, (a) very low or very high concentrations or activities of coagulation factors, (b) mutants of coagulation factors, (C) very low or very high concentrations or activities of inhibitors, (d) mutants of inhibitors or (e) antibodies against elements of the coagulation system.

In the clinical work day, screening tests are employed primarily for the diagnosis of hemorrhagic or thrombophilic diatheses and also for the monitoring of therapies with medicaments which influence the coagulation system. The determination of the APTT, for example, serves on the one hand for screening for defects of the part of the coagulation cascade which is started via the "intrinsic pathway" and opens into the common pathway, and which consists of the coagulation factors FVIII, FIX, FXI, FXII, pre-kallikrein, HMW kininogen, FV, FX, FII and fibrinogen. An APTT result above the normal range, i.e. a prolonged coagulation time, can point to a defect of one or more of these factors, for example to an FVIII defect, also known as hemophilia A. On the other hand, the APTT also reacts sensitively to the presence of anticoagulants, such as, for example, of heparin, and is therefore also used for the monitoring of heparin therapies.

For the medical assessment of a coagulation test result, the test result of a patient sample with a "reference range" (also called normal range) is compared. The reference range of a coagulation test is fixed by carrying out the test on a large number of obviously healthy persons (preferably $\geq 20$). Some of the healthy persons will have low test values, some somewhat higher, most values are scattered around a mean value. If the test results are plotted on the X-axis and the number of persons on the Y-axis, in the ideal case a normal distribution is obtained. Using statistical procedures, the lower and the upper reference limits are usually determined, within which lie 90% of all healthy persons. As a rule, the reference range (normal range) thus comprises 90% of the values which were measured in healthy reference persons. Under certain circumstances, it is necessary to lay down various, for example age- or sex-dependent, reference ranges for a test.

If the result of a patient sample differs from the reference range, this may argue for a disturbance of the hemostatic equilibrium. A difference from the reference range of the APTT in the direction of longer coagulation times can, for example, indicate a factor VIII defect; a difference from the reference range of the PT in the direction of shorter coagulation times can, for example, indicate an increased factor II level, for example caused by a mutation in the promoter region of the factor II gene, which leads to increased factor II synthesis.

In the case of the monitoring of therapies with medicaments which influence the coagulation system, such as, for example, therapy with anticoagulants, it is a matter of the adjustment of the coagulation system of the patient to a certain target size. In this connection, the medication is changed until the test result of the patient sample lies in a defined, "therapeutic" range. The therapeutic range is as a rule determined in extensive clinical studies. In this connection, a maximum of therapeutic efficiency and a minimum of undesired side effects is set in relation to a certain range of values of a diagnostic test result or to a certain concentration range of the medicament.

The medicinal inhibition of the coagulability by the administration of anticoagulants, such as, for example, heparin, plays an important role in the prophylaxis or therapy of thromboembolic events. The efficiency of the anticoagulation is measured in the clinic by the number of undesired thromboembolic events. Undesired side effects of the anticoagulants can be hemorrhagic complications. The therapeutic range of values of a test which is suitable for the control of an anticoagulatory therapy is thus the measurement range of the test in which a minimum of thromboembolic and of hemorrhagic complications was observed in a clinical study.

It is known that the test results of hemostaseological tests are subject to variance and are therefore not comparable without problems. This variance is based, inter alia, on the use of various reagents and on differences in the technical determination of the coagulation time. For instance, a large number of tissue thromboplastins are available for the determination of the prothrombin time (PT). The PT of one and the same plasma sample can differ, depending on the tissue thromboplastin used, up to a factor of 2. Even when using a specific tissue thromboplastin, the coagulation time of a sample varies depending on the manufacturer, depending on the batch of a manufacturer or, under certain circumstances, even depending on a bottle of an individual batch. Furthermore, in the automatic determination of a coagulation time the measuring apparatus itself and the manner of coagulation detection exert an influence on the coagulation time. The measurement of one and the same sample using the same tissue thromboplastin in different apparatuses yields different test results.

In practice, each laboratory sets up local, internal laboratory reference and therapeutic ranges for a coagulation test used. To make possible an assessment of a test result by the treating physician, beside the actual test result information on the local reference ranges or the therapeutic ranges of a test must also additionally be supplied.

In the prior art, various standardization procedures are known which have the aim of compensating reagent-, manufacturer-, batch- and apparatus-dependent differences between the test results. The standardization of test results and the comparability of test results is of particular advantage for various reasons. On the one hand, it is possible thereby to compare test results which have been determined in different laboratories in the context of clinical studies globally with one another, on the other hand, the interpretation of patient test results is significantly simplified.

Customary standardization procedures are based on normal plasma dilutions (standardization in % of the norm, e.g. in the Quick test), ratio formation (standardization in ratio), and normalized ratio formation (International Normalized Ratio INR in the prothrombin test).

When using normal plasma dilutions, first a reference plasma pool (normal plasma pool) is prepared from the plasma of, as a rule, at least 20 obviously healthy donors. The activity or the hemostatic potential of this standard is defined as 100% of the norm. Dilutions of this standard plasma in a suitable matrix are prepared. For example, one part of normal plasma pool is mixed with two parts of a suitable buffer (1:2 dilution) and defined as an activity of 33.33% of the norm. By measurement of the normal plasma pool and of the series of dilutions of this pool with the aid of the test system to be standardized, a reference curve (calibration curve) is plotted by assigning to the measured raw values the defined activities in % of the norm. For patient samples, the raw value can then be measured in the standardized test system and finally converted, with the aid of the reference curve, to a calibrated value or a standardized test result, namely in % of the norm.

In the standardization procedures which are based on ratio formation, in principle two procedures are to be differentiated. In the first case, two different tests are carried out for each sample and the results are written in a ratio to one another. Reference ranges and therapeutic ranges can be determined for this ratio. In the second case, the result of a patient sample and the result of a normal plasma pool are determined in the same test system and the ratio is formed. Such a procedure exists, for example, for the standardization of the prothrombin time (PT), where the prothrombin ratio (PR) indicates the ratio of the PT of a patient sample to the PT of a normal plasma ($PR=PT_{patient}/PT_{normal}$)

For further standardization of the prothrombin ratio (PR), a reference thromboplastin was created by the World Health Organization (WHO), to which prothrombin ratios determined using other thromboplastins can be adjusted so that the determined PR can be converted to an International Normalized Ratio (INR). As a measure of the sensitivity of a thromboplastin reagent in comparison to the sensitivity of the WHO thromboplastin reagent, a correction factor was introduced, the International Sensitivity Index (ISI), so that the INR can be calculated according to the formula $INR=PR^{ISI}$.

For the WHO thromboplastin reagent, the ISI value is defined as 1.0, so that INR is =PR. For all other thromboplastins, ISI values are communicated by the manufacturers.

In spite of these efforts, to date no convincing standardization is possible in one series of coagulation tests, e.g. in the case of the activated partial thromboplastin time (APTT), the thrombin time (TT), the batroxobin time (BT) or the ecarin time (ECT). Admittedly, in the past there were attempts to standardize the APTT analogously to the prothrombin time by ratio formation between the APTT of a patient sample and the APTT of a normal plasma, and it was attempted to define the therapeutic range for the APTT ratio to 1.5-2.5. However, the procedure has never gained acceptance, as even the standardized values (APTT ratio) have too great a variance in order to guarantee an acceptable comparability of measured results [Brill-Edwards, P. et al (1993) Establishing a therapeutic range for heparin therapy. Ann Intern Med. 119 (2), 104-109]. Alternatively, in analogy to the calculation of the INR for the prothrombin time, it was attempted to establish standardization of the APTT by means of a reference reagent [Reed, S. V. et al. (1994) An attempt to standardize the APTT for heparin monitoring, using the P.T. ISI/INR system of calibration. Results of a 13 centre study. Thromb. Res. 74 (5), 515-522; van der Velde, E. A. & Poller, L. (1995) The APTT monitoring of heparin—the ISTH/ICSH collaborative study. Thromb Haemost. 73 (1), 73-81.]. The results, however, were largely disappointing, as it was likewise not possible to achieve any acceptable comparability of the measured results.

The lacking standardization of the coagulation tests in the monitoring of therapies using anticoagulants is particularly problematical. The problematology is intended to be shown here exemplarily by example of the monitoring of a heparin treatment with the aid of the APTT.

Heparin inhibits the coagulation system in an immediate and concentration-dependent manner. Unfractionated heparin (UFH) and low molecular weight heparins (LMWH) are used. Heparin therapy is carried out in the case of thromboembolic events which have already occurred or are present in acute form. Heparin prophylaxis should prevent the occurrence of thrombolic events. The heparin levels (in IU/ml) to be adjusted are customarily indicated as therapeutic ranges both for heparin therapy and for heparin prophylaxis. A therapeutic range of 0.3-0.7 IU/ml thus applies for heparin therapy and a therapeutic range of approximately 0.05-0.25 IU/ml for heparin prophylaxis.

Therapy and prophylaxis with heparin, in particular with unfractionated heparin, can on the one hand be monitored using procedures which measure the heparin level directly, and on the other hand also using coagulation tests which measure the influence of the heparin on the coagulability of the blood.

The direct determination of the heparin level is carried out, for example, by means of "factor Xa-based or anti-Xa procedures", in which the factor Xa-inhibiting activity of a patient sample is measured. This test can be standardized with the aid of International Heparin Standards and accordingly yields a standardized, comparable result in the form of a concentration value in International Units per milliliter (IU/ml). This procedure for the determination of the heparin level, however, has not gained acceptance in routine diagnosis, as the necessary test system is expensive and not available in many laboratories.

Alternatively, the monitoring of a heparin therapy is carried out nowadays by means of the measurement of the APTT. In the monitoring of a heparin therapy with the aid of the APTT, it is a matter of controlling the heparin administration such that an APTT result in the therapeutic range results. Since on account of the test system-dependent variance of the APTT values there is no standardized therapeutic range for APTT values, it is necessary for each test system to determine the therapeutic range. For the determination of the therapeutic range of the APTT test for unfractionated heparin, there are basically two possibilities [Nelson, D. E. (1999) Current considerations in the use of the APTT in monitoring unfractionated heparin. Clin Lab Sci. 12 (6), 359-64; Olson, J. D. et al. (1998) College of American Pathologists Conference XXXI on laboratory monitoring of anticoagulant therapy: laboratory monitoring of unfractionated heparin therapy. Arch Pathol Lab Med. 122 (9), 782-98]:

In the "ex vivo procedure", plasma samples of a group of heparinized patients are taken. The heparin level in IU/ml of each sample is determined using a factor Xa test and the APTT is determined using a test system. Subsequently, a linear regression between the two data sets (heparin level in IU/ml and APTT in s) is carried out. The therapeutic range in the APTT test system is the range of values which corresponds to the heparin concentration range from 0.3-0.7 IU/ml (see also Example 1). The ex vivo procedure is comparatively involved and also expensive. It assumes a relatively large number of available patient and normal samples and the availability of a factor Xa-based procedure for the determination of the heparin level.

On account of the aforementioned disadvantages of the ex vivo method, an "in vitro" procedure has been established in laboratory practice. In this procedure for the determination of the therapeutic range of an APTT test, a normal plasma pool is treated ("spiked") with standardized amounts of heparin and the APTT of the samples thus prepared is measured. It is unconditionally to be taken into account, however, that an in vitro sample (e.g. heparin-spiked normal plasma) can lead to other coagulation times compared with an ex vivo sample with identical heparin level. For the determination of the therapeutic range of an APTT test with the aid of an in vitro procedure, other limits must therefore be taken into consideration for the heparin content of the calibration samples. In publications, an ex vivo heparin concentration range of 0.3-0.7 IU/ml is assigned an in vitro range of 0.2-0.4 IU/ml. The in vitro procedure for the determination of the therapeutic APTT range for the heparin therapy is an approximation procedure with limited informative value.

Up to now, tests for the determination of the APTT, the TT, the BT and the ECT yielded a coagulation time which alone is evaluated in seconds, the result always depending on the local test system, i.e. on the reagent, batch of reagents, variance from bottle to bottle, test procedure, automation, measuring apparatus, measurement procedures and evaluation procedures. The global comparability of the test results is thus scarcely afforded.

The present invention is thus based on the object of making available an in vitro procedure which makes possible the standardization of coagulation tests and thus guarantees the global comparability of test values which have been determined with the aid of different (local) test systems.

The solution according to the invention consists in the making available of the articles and procedures described in the claims.

The term "coagulation time" is to be understood in the sense of the present invention as meaning a test result of an in vitro coagulation test, in which the timespan from the addition of an activator reagent and/or of $Ca^{2+}$ ions to a sample or a sample mixture is measured in seconds [s] up to the detectable formation of a fibrin clot or, if a chromogenic substrate is used, the timespan from the addition of an activator reagent and/or $Ca^{2+}$ ions to the sample up to the achievement of a defined absorption change rate. The use of a chromogenic substrate is known, for example, in methods for the determination of the PT (see, for example, EP 14 039 A1)

The procedure according to the invention makes possible the determination of a standardized coagulation time of a sample by converting the measured coagulation time of the sample (primary test result, actual value) to a standardized coagulation time (standardized test result, nominal value) with the aid of a calibration curve (reference curve)

A procedure for the determination of a standardized coagulation time from the group consisting of prothrombin time (PT), activated partial thromboplastin time (APTT), thrombin time (TT), batroxobin time (BT) and ecarin time (ECT) is particularly preferred.

The availability of at least two calibrators is necessary for plotting the calibration curve, where for each calibrator a discrete standard coagulation time in seconds [s] was predetermined. The number of calibrators which can be employed is not restricted upwardly.

The fixing (predetermination) of the standard coagulation time of a calibrator can be carried out in various ways. One possibility is to determine the standard coagulation time of a calibrator in a single run of a coagulation test, this test run taking place under the defined conditions of a specific, local coagulation test system, i.e. the standard coagulation time is measured using a specific activator reagent of a specific batch of reagents on a specific measuring apparatus. For example, the use of a specific APTT reagent batch for the determination of the APTT of a calibrator and the assignment of the APTT measured under these specific conditions as an APTT standard coagulation time is possible. Another possibility is to fix the standard coagulation time of a calibrator by averaging a plurality of test results of a coagulation test. Preferentially, different activator reagent batches are used for this. However, alternative activator reagent types can also be used, such as, for example, different APTT activators (kaolin or ellagic acid or silica etc.). The mean value, for example, is then formed from the coagulation times measured in the individual test runs and assigned to the calibrator as a standard coagulation time. Preferentially, the standard coagulation times of all calibrators which are to be used for the plotting of a reference curve are fixed and assigned in the same manner.

Preferentially, for plotting the reference curve a kit of calibrators is used which are distinguished by different hemostatic potentials and thus by different standard coagulation times. Another preferred kit contains a single calibrator (stock calibrator) with a fixed, defined standard coagulation time, which is diluted with different volumes of a dilution liquid, e.g. a buffer solution, whereby a series of calibrators can be prepared which are likewise distinguished by different hemostatic potentials. Preferentially, the dilution fluid is contained in a kit according to the invention together with the stock calibrator.

The plotting of the calibration curve is carried out by determining the coagulation times of the calibrators in the same local test system as the coagulation time of a sample to be determined. By means of the assignment of the predetermined standard coagulation times of the calibrators to the accompanying coagulation times measured and interpolation or extrapolation, a reference curve is plotted, where, for example, the standard coagulation time (nominal value) is plotted on the x-axis and the measured coagulation time (actual value) is plotted on the y-axis. The measured coagulation time of a sample is converted to a standardized coagulation time with the aid of the reference curve.

Particularly preferably, calibrators are used which have the same matrix as the sample, whose coagulation time should be standardized. The present procedure is particularly suitable for the standardization of the coagulation times of plasma samples, of human or animal origin, which can be treated with citrate. For this reason, calibrators are to be preferred which are likewise based on plasma, preferably based on a plasma pool, where in this case, for example, they can also be mixtures of human with nonhuman plasma. By mixing human plasma with different proportions of, for example, rabbit and/or bovine plasma and measuring the coagulation time of such a plasma mixture, the person skilled in the art can prepare calibrators for use in the procedure according to the invention. The plasma calibrators can additionally contain substances which are customarily used in the preparation of plasma calibrators or controls. These include, for example, buffer substances such as, for example, TRIS or HEPES, anticoagulatory substances such as citrate, and stabilizers, such as, for example, dextran, and preservatives such as, for example, sodium azide. For use in the procedure according to the invention, the calibrators can be prepared in liquid, frozen or freeze-dried condition.

A particular embodiment of the procedure according to the invention relates to the determination of a standardized coagulation time of a sample which contains a substance which influences the coagulation system. Substances of this type can be anticoagulatory substances which are administered to a patient in the course of an anticoagulation therapy or which are tested for use in an anticoagulation therapy in the course of a clinical trial or in a comparable research study. These can be, for example, those medicaments or substances having anticoagulatory action, such as heparins, comprising unfractionated, high molecular weight heparins (UFH), fractionated, low molecular weight heparins (LMWH), semi- or fully synthetic heparinoids (such as, for example, Danaparoid or Orgaran®) or pentasaccharides, such as Fondaparinux; vitamin K antagonists, such as, for example, coumarin derivatives, or direct thrombin inhibitors, such as hirudin, argatroban or melagatran. Furthermore, they can be natural or synthetic factor Xa inhibitors, where in the case of many natural factor Xa inhibitors recombinant variants can also be used. Examples of natural factor Xa inhibitors which are otherwise often isolated from the saliva of hematophagous animals, are antistasin, a polypeptide from the Mexican leech *Haementeria officinalis*, the Tick Anticoagulant Peptide, a polypeptide from the soft tick *Ornithodorus moubata*, yagin, a polypeptide from the leech *Hirudo medicinalis* or draculin from the vampire bat *Desmodus rotundus*. The synthetic factor Xa inhibitors belong to various classes and are different in diamidino- and bisbasic FXa inhibitors, monobenzamidine FXa inhibitors and nonbenzamidine FXa inhibitors. In the case of the determination of the coagulation time of samples of anticoagulated patients, it is a matter, inter alia, of determining whether the anticoagulant concentration in the blood or plasma of the patient lies in the therapeutic range.

For the standardization of the coagulation time of such anticoagulated samples, the use of a calibrator is recommended which contains a defined amount of an anticoagulatory substance which has an anticoagulatory function in vitro. For the standardization of the coagulation time of samples of heparin-treated patients, for example, the use of a calibrator is recommended which has been spiked with a defined amount of heparin. Preferentially, such a calibrator has a heparin concentration of between 0.1 and 1.0 IU/ml.

Figure 1:
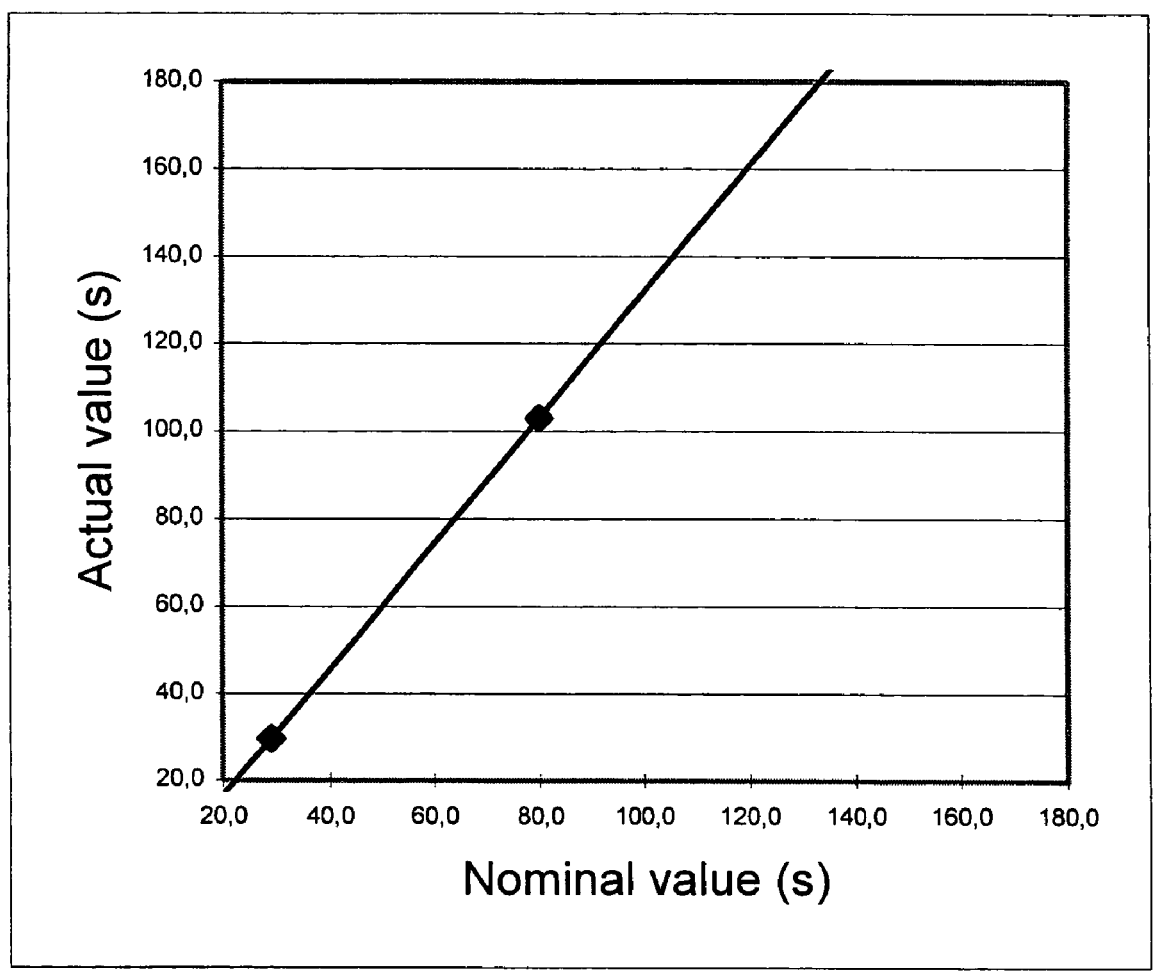
FIG. 1 is a reference curve plotted by extrapolation of the standard APTT (nominal value) and the APTT measured in parallel to the plasma samples (actual value) for the two calibrators, under normal and heparin-treated conditions.

The following exemplary embodiments serve for the illustration of the procedure according to the invention and are not to be understood as a restriction.

EXAMPLES

Example 1

Determination of the Therapeutic Range for Heparin in an APTT Test System (Ex Vivo Method)

Plasma samples of heparin-treated patients and a normal plasma pool were used. For each sample, the heparin level in IU/ml was determined against a suitable heparin standard in a factor Xa test (Berichrom® Heparin, Dade Behring Marburg GmbH, Margurg, Germany). Moreover, the APTT of each sample was determined using an activator reagent (phospholipids and ellagic acid, Dade® Actin® FSL reagent, Dade Behring Margurg GmbH, Marburg, Germany) of the same batch. The results of these measurements are listed in Table 1.

TABLE 1

|  | Heparin [IU/ml] | APTT [seconds] |
| --- | --- | --- |
| Normal pool | 0.00 | 29.4 |
| Patient | 0.60 | 75.9 |
| Patient | 0.60 | 75.9 |
| Patient | 0.01 | 42.5 |
| Patient | 0.02 | 57.4 |
| Patient | 0.02 | 34.3 |
| Patient | 0.04 | 36.2 |
| Patient | 0.05 | 33.9 |
| Patient | 0.05 | 34.4 |
| Patient | 0.05 | 58.1 |
| Patient | 0.05 | 34.5 |
| Patient | 0.06 | 49.6 |
| Patient | 0.06 | 27.1 |
| Patient | 0.06 | 45.5 |
| Patient | 0.07 | 27.1 |
| Patient | 0.07 | 58.8 |
| Patient | 0.07 | 84.2 |
| Patient | 0.08 | 36.4 |
| Patient | 0.10 | 46.5 |
| Patient | 0.11 | 48.1 |
| Patient | 0.12 | 52.3 |
| Patient | 0.13 | 46.5 |
| Patient | 0.17 | 39.5 |
| Patient | 0.18 | 42.8 |
| Patient | 0.19 | 62.8 |
| Patient | 0.22 | 55.3 |
| Patient | 0.22 | 67.9 |
| Patient | 0.23 | 75.2 |
| Patient | 0.24 | 66.4 |
| Patient | 0.25 | 49.1 |
| Patient | 0.27 | 55.3 |
| Patient | 0.27 | 25.8 |
| Patient | 0.31 | 70.6 |
| Patient | 0.31 | 41.0 |
| Patient | 0.32 | 57.5 |
| Patient | 0.32 | 37.3 |
| Patient | 0.33 | 55.3 |
| Patient | 0.34 | 40.1 |
| Patient | 0.34 | 51.1 |
| Patient | 0.34 | 72.4 |
| Patient | 0.36 | 64.8 |
| Patient | 0.36 | 51.3 |
| Patient | 0.37 | 75.1 |
| Patient | 0.38 | 53.7 |
| Patient | 0.39 | 70.6 |
| Patient | 0.40 | 51.4 |
| Patient | 0.41 | 72.3 |
| Patient | 0.43 | 83.6 |
| Patient | 0.43 | 70.2 |
| Patient | 0.45 | 116.4 |
| Patient | 0.49 | 63.9 |
| Patient | 0.51 | 64.4 |

TABLE 1-continued

|  | Heparin [IU/ml] | APTT [seconds] |
|---|---|---|
| Patient | 0.52 | 69.3 |
| Patient | 0.54 | 59.0 |
| Patient | 0.69 | 73.9 |

With the aid of the software Microsoft® Excel Version 97 SR-2 (Microsoft Corporation, Redmond, USA), a linear regression of the two data sets was carried out:

APTT [s]=$a$×heparin [IU/ml]+$b$ a=58.47 b=40.39

With the aid of the lines of best fit, the APTT range of values was determined which corresponds to the generally known therapeutic range of the ex vivo heparin level of 0.3-0.7 IU/ml:

TABLE 2

| Heparin [IU/ml] | APTT [s] according to regression line |
|---|---|
| 0.3 | 57.9 |
| 0.7 | 81.3 |

Accordingly, the therapeutic range comprised APTT values from 57.9 to 81.3 seconds.

Example 2

Preparation of Heparin Calibrators and Fixing of their Discrete Standard APTTs for Use in a Procedure According to the Invention for the Standardization of the APTT Calibrator 1: Normal Plasma Pool Plasma from 20 healthy donors was collected in 3.2% sodium citrate, pooled, buffered with 50 mM HEPES buffer (pH 7.5), stabilized using suitable stabilizers, filled into 1 ml aliquots and lyophilized. For use, the calibrator is reconstituted using 1 ml of double-dist. water.

Calibrator 2: Heparin-Plasma Pool

A defined amount of unfractionated heparin (Liquemin®, Roche Deutschland Holding GmbH, Grenzach-Wyhlen, Germany) was added to a suitable stabilizer solution such that a final concentration of 0.6 IU/ml was achieved. With the aid of a factor Xa test (Berichrom® Heparin, Dade Behring Marburg GmbH, Marburg, Germany) calibrated using an international heparin standard, the heparin activity of the heparin solution was determined in an automatic coagulation measuring apparatus. The factor Xa test was calibrated using an international heparin standard. The heparin solution was filled into 1 ml aliquots and lyophilized. For use, the calibrator was reconstituted with 1 ml of normal plasma pool.

For the determination of the standard APTT of the two calibrators, the APTT of each plasma was determined using an activator reagent (phospholipids and ellagic acid, Dade® Actin® FSL reagent, Dade Behring Marburg GmbH, Marburg, Germany) of the same batch on the same coagulation measuring apparatus (BCS® coagulation analyzer, Dade Behring Marburg GmbH, Marburg, Germany). The following APTT values were determined:

TABLE 3

| Normal plasma pool | 29 s |
|---|---|
| Heparin plasma pool | 80 s |

The APTT value was now assigned to the corresponding calibrator as a discrete standard APTT (nominal value)

Example 3

Determination of Standardized APTT Values with the Aid of the Procedure According to the Invention The APTTs of the two calibrators (see Example 2) and of plasma samples of heparin-treated patients were determined using an activator reagent (phospholipids and ellagic acid, Dade® Actin® FSL reagent, Dade Behring Marburg GmbH, Marburg, Germany) of any desired batch on any desired coagulation measuring apparatus.

For the two calibrators, the following pairs of values resulted from the assignment of the predetermined standard APTT (nominal value) and the APTT measured in parallel to the plasma samples (actual value)

TABLE 4

|  | Nominal value [s] | Actual value [s] |
|---|---|---|
| Normal plasma pool | 29 | 29.6 |
| Heparin plasma pool | 80 | 103.0 |

A reference curve was plotted by extrapolation of the two pairs of values (FIG. 1)

With the aid of this reference curve, the measured, primary APTT values of the plasma samples were now converted to standardized APTT values (see Tab. 5). The plotting of the reference curve and the conversion of the measured values was carried out automatically by the coagulation measuring apparatus.

TABLE 5

| Measured APTT [s] | Standardized APTT [s] |
|---|---|
| 29.6 | 29.0 |
| 103.0 | 80.0 |
| 103.0 | 80.0 |
| 50.2 | 43.3 |
| 67.2 | 55.1 |
| 44.8 | 39.6 |
| 46.6 | 40.8 |
| 41.2 | 37.1 |
| 35.3 | 33.0 |
| 58.3 | 48.9 |
| 35.3 | 33.0 |
| 59.7 | 49.9 |
| 28.8 | 28.4 |
| 51.4 | 44.1 |
| 28.7 | 28.4 |
| 68.2 | 55.8 |
| 79.0 | 63.3 |
| 42.0 | 37.6 |
| 57.8 | 48.6 |
| 57.6 | 48.5 |
| 63.9 | 52.8 |
| 65.4 | 53.9 |
| 47.8 | 41.6 |
| 59.9 | 50.1 |
| 81.8 | 65.3 |
| 63.6 | 52.6 |
| 76.5 | 61.6 |

TABLE 5-continued

| Measured APTT [s] | Standardized APTT [s] |
|---|---|
| 105.9 | 50.0 |
| 93.8 | 73.6 |
| 59.8 | 54.4 |
| 66.1 | 27.8 |
| 27.9 | 67.3 |
| 84.7 | 39.6 |
| 44.9 | 64.2 |
| 80.2 | 37.3 |
| 41.5 | 52.8 |
| 63.9 | 37.1 |
| 41.2 | 49.3 |
| 58.8 | 78.2 |
| 100.4 | 65.8 |
| 82.6 | 53.0 |
| 64.1 | 66.6 |
| 83.7 | 56.6 |
| 69.3 | 71.0 |
| 90.0 | 54.4 |
| 66.1 | 74.2 |
| 94.7 | 82.5 |
| 106.6 | 69.7 |
| 88.2 | 93.5 |
| 122.4 | 66.5 |
| 83.5 | 59.9 |
| 74.1 | 83.8 |
| 108.5 | 82.6 |
| 106.7 | 76.9 |
| 98.5 | 82.0 |

Example 4

Therapeutic Ranges for Various Batches of an APTT Reagent Before and After Standardization of the APTT The APTTs of the two calibrators (see Example 2) and of plasma samples of heparin-treated patients were determined on a coagulation measuring apparatus using four different batches of an activator reagent (phospholipids and ellagic acid, Dade® Actin® FSL reagent, Dade Behring Marburg GmbH, Marburg, Germany) According to Example 3, each batch-dependent measured value of a sample was converted with the aid of the batch-dependent calibration curve to a standardized APTT value. The heparin concentration of the patient samples was determined in a factor Xa test (see Example 1).

Finally, both for the measured APTT values and for the standardized APTT values, the APTT range of values was determined which corresponds to the generally known therapeutic range of the ex vivo heparin level of 0.3-0.7 IU/ml (see Example 1).

TABLE 6

| | Therapeutic ranges (0.3–0.7 IU/ml of heparin ex vivo) APTT ranges of values in seconds | | | |
|---|---|---|---|---|
| | Batch 1 | Batch 2 | Batch 3 | Batch 4 |
| before standardization | 58–81 | 72–109 | 66–99 | 66–96 |
| after standardization | 66–96 | 64–95 | 67–99 | 66–96 |

Before standardization of the APTT values, the upper limits of the therapeutic ranges differ from one another from batch to batch by up to 35%. After standardization of the APTT values, the upper limits of the therapeutic ranges differ from one another from batch to batch only by up to 4%. The procedure according to the invention makes possible a unification of the therapeutic ranges, whereby the results of various test systems are directly comparable with one another after standardization.

The invention claimed is:

1. A method for the determination of a standardized coagulation time of a sample, comprising
   a) measuring the coagulation time of a sample in a test system:
   b) measuring the coagulation times of at least two calibrators, for which discrete standard coagulation times have been predetermined, in the same test system as used in step a);
   c) forming a calibration curve that plots the predetermined standard coagulation times of the calibrators versus the coagulation times of the calibrators measured in step b); and
   d) converting the coagulation time of the sample measured in step a) to a standardized coagulation time using the calibration curve formed in step c).

2. The method as claimed in claim 1 for the determination of a standardized coagulation time wherein the coagulation time is chosen from prothrombin time (PT), activated partial thromboplastin time (APTT), thrombin time (U), batroxobin time (BT) and ecarin time (ECT).

3. The method as claimed in claim 1, wherein the sample is a plasma sample.

4. The method as claimed in claim 1, wherein the calibrators are plasma-based.

5. The method as claimed in claim 1, wherein the calibrators are plasma pool-based.

6. The method as claimed in claim 1, wherein the sample contains a substance which influences the coagulability of the sample.

7. The method as claimed in claim 6, wherein the substance which influences the coagulability of the sample is an anticoagulatory substance.

8. The method as claimed in claim 7, wherein the anticoagulatory substance is chosen from heparin, heparinoids, hirudin, argatroban, melagatran and natural or synthetic factor Xa inhibitors.

9. The method as claimed in claim 7, wherein at least one calibrator contains a defined amount of an anticoagulatory substance.

10. The method as claimed in claim 9, wherein the anticoagulatory substance contained by at least one calibrator is heparin at a concentration of 0.1 to 1.0 IU per ml.

11. The method as claimed in claim 1, wherein the calibration curve is plotted with the aid of an interpolation or extrapolation procedure.

* * * * *